United States Patent

Wiedemann et al.

[11] 4,171,446
[45] Oct. 16, 1979

[54] INDAZOLE COMPOUNDS

[75] Inventors: Fritz Wiedemann, Weinheim-Lützelsachsen; Wolfgang Kampe, Heddesheim, both of Fed. Rep. of Germany

[73] Assignee: Boehringer Mannheim GmbH, Mannheim, Fed. Rep. of Germany

[21] Appl. No.: 790,646

[22] Filed: Apr. 25, 1977

[30] Foreign Application Priority Data

Apr. 30, 1976 [DE] Fed. Rep. of Germany ....... 2619165

[51] Int. Cl.$^2$ .................. C07D 231/56; C07D 405/12
[52] U.S. Cl. ..................................... 548/372; 548/371; 424/273 B
[58] Field of Search ................................ 548/371, 372

[56] References Cited

U.S. PATENT DOCUMENTS 2,645,642  7/1953  Adams et al. ...................... 548/371

FOREIGN PATENT DOCUMENTS 7631M  1/1970  France ..................................... 548/372

Primary Examiner—John M. Ford
Assistant Examiner—Natalia Harkaway
Attorney, Agent, or Firm—Sprung, Felfe, Horn, Lynch & Kramer

[57] ABSTRACT

Indazole compounds of the formula

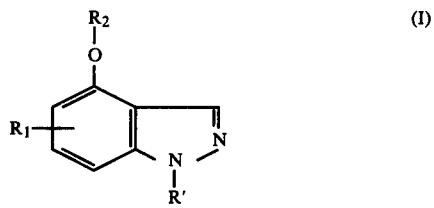

wherein
  $R_1$ is hydrogen or lower alkyl,
  $R'$ is hydrogen or acyl, e.g., alkanoyl, and
  $R_2$ is benzyl or a radical of the general formula

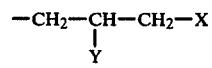

in which X is a reactive residue and Y is hydroxyl or X and Y together represent oxygen and, when R' is an acyl radical, $R_2$ can also be hydrogen: are valuable intermediates for the preparation of pharmacologically active compounds, e.g., adrenergic β-receptor active 3-indazolyl-(4)-oxy-propan-2-ol-amines.

14 Claims, No Drawings

INDAZOLE COMPOUNDS

The present invention is concerned with new indazole compounds and with the preparation thereof.

The new derivatives of indazole according to the present invention are compounds of the formula:

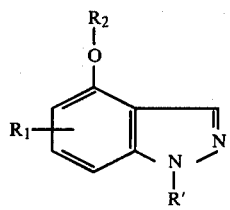
(I)

wherein
$R_1$ is hydrogen or lower alkyl,
$R'$ is hydrogen or acyl, e.g., alkanoyl, and
$R_2$ is benzyl or a radical of the general formula $$-CH_2-CH(Y)-CH_2-X$$

in which X is a reactive residue and Y is hydroxyl or X and Y together represent oxygen and, when $R'$ is an acyl radical, $R_2$ can also be hydrogen.

We have found that the compounds of the general formula (I) are valuable intermediates for the preparation of useful, pharmacologically-active compounds, for example, as disclosed in German Patent Application No. P 26 19 164.0, corresponding to U.S. Ser. No. 790,648, filed Apr. 25, 1977. Thus, by simple reactions of compounds of the general formula (I), in which $R_2$ is a —$CH_2$—$CH(Y)$—$CH_2$—X radical, with lower alkylamines, such as isopropylamine or tert.-butylamine, there are obtained 3-indazolyl-(4)-oxy-propan-2-ol-amines which can bring about an inhibition of adrenergic β-receptors and can, therefore, be used for the treatment and prevention of a recurrence of cardiac and circulatory diseases. Thus, for example, by the reaction of 1-acetyl-4-(2,3-epoxypropoxy)-indazole with isopropylamine, there is obtained 1-[indazolyl-(4)-oxy]-3-isopropylaminopropan-2-ol. By reaction with other appropriate compounds, there can also be obtained circulatory-active and anti-allergically effective compounds.

The new compounds of general formula (I) according to the present invention can be obtained, for example, by one of the following methods:

(a) reaction of a 4-hydroxy-indazole of the general formula:

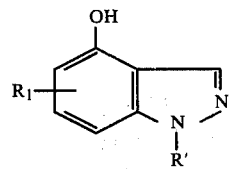
(II)

in which $R_1$ and $R'$ have the same meanings as above, with a compound of the general formula:

$$Z-R_2$$  (III), in which $R_2$ has the same meaning as above and Z is a reactive residue; or (b) for the case in which $R_2$ in general formula (I) is a hydrogen atom or a benzyl radical, a compound of the general formula:

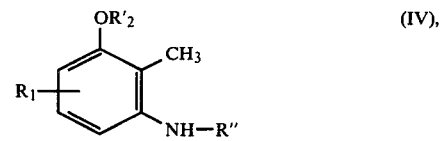
(IV), in which $R_1$ has the same meaning as above, $R'_2$ is a benzyl radical and $R''$ is an acyl radical, is nitrosated, cyclized and subsequently, if desired, the benzyl or acyl radical is split off;

whereafter, if desired, the compound obtained of general formula (I) is subsequently converted into a different compound of general formula (I).

The lower alkyl radicals of the substituent $R_1$ can contain up to 4 carbon atoms, the methyl radical being preferred.

The protective acyl radicals $R'$ and $R''$ are to be understood to be radicals containing up to 7 carbon atoms, the acetyl and benzoyl radicals being preferred.

Reactive residues X and Z in the compounds of general formulae (I) and (III) can be, for example, acid residues, especially those of hydrohalic acids and of sulphonic acids, such as methane-sulphonic acid and p-toluene-sulphonic acid.

The reactions according to process (a) are advantageously carried out in an organic solvent which is inert under the selected reaction conditions, with the addition of a base at ambient temperature or by heating. As solvent, for the purpose of retaining an acyl radical $R'$, it is preferable to use aprotic solvents, such as dimethyl formamide and dimethyl sulphoxide, and as bases, there can be used, for example, sodium hydride, as well as alkali metal carbonates.

As compounds of general formula (III), there can be used esters of 2,3-epoxypropanol with hydrohalic acids, such as epichlorohydrin and epibromohydrin, as well as with sulphonic acids, such as methane-sulphonic acid and p-toluene-sulphonic acid.

Compounds of general formula (II) in which $R'$ is an acyl radical are new. These are preferably used in process (a) since the acyl radical protects the indazole nitrogen atom against alkylation. They can be prepared according to process (b). According to this process, 3-acylamino-2-methyl-phenyl-benzyl ethers of general formula (IV) are nitrosated in an aprotic solvent, for example toluene, in the presence of the anhydride and of an alkali metal salt of the acid corresponding to the acyl radical, for example with isoamyl nitrite, and then cyclized by heating. Subsequently, the benzyl radical of the compound obtained can be easily split off hydrogenolytically in the presence of a noble metal catalyst.

An indazole synthesis analogous to process (b) is described in German Pat. No. 2,155,545.

The subsequent conversion of compounds of general formula (I) into other compounds of general formula (I) can be carried out by known methods. Thus, the 4-(2,3-epoxypropoxy)-indazoles obtained according to process (a) can be converted, by the addition of strong acids, into reactive compounds of general formula (I) in which X is a reactive residue and Y is a hydroxyl group or, vice versa, the epoxides can be obtained from the latter by splitting off acids with strong bases.

Furthermore, compounds of general formula (I) in which the reactive residue X is a methane-sulphonyloxy or a p-toluene-sulphonyloxy radical can be obtained by reacting 4-(2,3-epoxypropoxy)-indazoles with methanesulphonyl chloride or with p-toluene-sulphonyl chloride in the presence of a tertiary amine. As solvents, there can be used inert organic solvents, such as toluene, diethyl ether or tetrahydrofuran, and as tertiary amines there can be used, for example, triethylamine or N-ethyldiisopropylamine, as well as pyridine, in which case, the latter can also function as the solvent. The preferred temperature range for these reactions is from $-30°$ C. to ambient temperature.

The 4-(2,3-epoxypropoxy)-indazoles hereby used can be obtained by hydrolysis of the corresponding acetonides which are obtainable by the reaction of compounds of general formula (II) with glycerol acetonide p-toluenesulphonate analogously to process (a).

Furthermore, in the case of compounds of general formula (I) in which R' is an acyl radical, this acyl radical can be removed selectively under mild conditions by aminolysis or hydrolysis, i.e., without changing the other functional groups present.

The following Examples are given for the purpose of illustrating the present invention:

EXAMPLE 1

1-Acetyl-4-benzyloxy indazole

A mixture of 64 g. (3-acetamino-2-methyl-phenyl)-benzyl ether, 25 g. sodium acetate, 69 ml. acetic anhydride, 50 ml. isoamyl nitrite and 2 liters toluene is stirred for 15 to 20 hours at 80° to 90° C. After cooling the reaction mixture to 10° C., salts are filtered off with suction and the filtrate is evaporated to dryness in a vacuum. By trituration of the residue with 300 ml. methanol, there are obtained 47.5 g. of almost colorless crystals of 1-acetyl-4-benzyloxy-indazole; m.p. 97° C.

The (3-acetamino-2-methyl-phenyl)-benzyl ether used as starting material can be obtained in two reaction stages, as follows:

(3-Amino-2-methyl-phenyl)-benzyl ether

By the reduction of (2-methyl-3-nitrophenyl)-benzyl ether with hydrazine hydrate and Raney nickel in methanol, the crude product is obtained in the form of a green oil.

(3-Acetamino-2-methyl-phenyl)-benzyl ether

Acetylation of the compound obtained in (a) above with acetic anhydride in toluene. The product is obtained in the form of colorless crystal which melt at 142°-143° C., after recrystallization from toluene.

EXAMPLE 2

1-Acetyl-4-benzyloxy-6-methyl-indazole

A mixture of 149 g. (3-acetamino-2,5-dimethyl-phenyl)-benzyl ether, 50 g. sodium acetate, 138 ml. acetic anhydride, 50 ml. isoamyl nitrite and 3 liters toluene is stirred for 15 to 20 hours at 80° to 90° C. After cooling, the reaction mixture is filtered with suction and the filtrate is evaporated to dryness in a vacuum. The residue is taken up in about 300 ml. methanol, whereupon the product crystallizes in the cold. There are obtained 103 g. 1-acetyl-4-benzyloxy-6-methyl-indazole in the form of yellowish crystals; m.p. 91°-93° C.

The (3-acetamino-2,5-dimethyl-phenyl)-benzyl ether used as starting material in Example 2 is prepared from 2,5-dimethyl-3-nitrophenol by the following reactions:

(2,5-Dimethyl-3-nitrophenyl)-benzyl ether

A mixture of 433 g. 2,5-dimethyl-3-nitrophenol, 360 g. potassium carbonate, 326 ml. benzyl chloride and 2 liters dimethyl formamide is stirred overnight at 50° C. The reaction mixture is then filtered with suction and the filtrate is evaporated to dryness in a vacuum. The residue is poured on to 4 liters of ice-water and, after suction filtration and drying in the air, there are obtained 668 g. of yellowish crystals; m.p. 66°-68° C.

(3-Amino-2,5-dimethyl-phenyl)-benzyl ether

The above-described nitro compound is reduced with hydrazine hydrate and Raney nickel in methanol. The crude product is obtained in good yield in the form of a brown oil.

(3-Acetamino-2,5-dimethyl-phenyl)-benzyl ether

Acetylation of the above-described amino compound with acetic anhydride in toluene gives colourless crystals which, after recrystallisation from toluene, melt at 169°-171° C.

In an analogous manner, there are obtained:
(a) from (3-acetamino-2,6-dimethyl-phenyl)-benzyl ether (m.p. 161°-162° C.) (prepared via (2,6-dimethyl-3-nitrophenyl)-benzyl ether and (3-amino-2,6-dimethyl-phenyl)-benzyl ether), 1-acetyl-4-benzyloxy-5-methyl-indazole; m.p. 108°-109° C.
(b) from (3-acetamino-2,4-dimethyl-phenyl)-benzyl ether (m.p. 160°-162° C.) (prepared via (2,4-dimethyl-3-nitrophenyl)-benzyl ether (m.p. 65°-67° C.) and (3-amino-2,4-dimethyl-phenyl-benzyl ether), 1-acetyl-4-benzyloxy-7-methyl-indazole; m.p. 90°-92° C.
(c) from (2-methyl-3-acetamino-5-ethyl-phenyl)-benzyl ether; m.p. 139°-140° C. (prepared via (2-methyl-3-nitro-5-ethyl-phenyl)-benzyl ether and (2-methyl-3-amino-5-ethyl-phenyl)-benzyl ether), 1-acetyl-4-benzyloxy-6-ethyl-indazole; m.p. 109,5°-110,5° C.

EXAMPLE 3

4-Benzyloxy-6-methyl-indazole 0.5 g. 1-Acetyl-4-benzyloxy-6-methyl-indazole is left to stand for 1 hour at ambient temperature in 10 ml. isopropylamine. The reaction mixture is then evaporated to dryness in a vacuum and the residue obtained is recrystallized from methanol-water, with the use of active charcoal. There is obtained 0.2 g. 4-benzyloxy-6-methylindazole in the form of colourless crystals; m.p. 105°-107° C.

In an analogous manner, there are obtained 4-benzyloxy-5-methyl-indazole (m.p. 94°-95° C.); 4-benzyloxy-7-methyl-indazole (m.p. 175°-177° C.), and 4-benzyloxy-6-ethyl-indazole.

EXAMPLE 4

1-Acetyl-4-hydroxy-indazole

By the hydrogenolysis of 1-acetyl-4-benzyloxyindazole in the presence of palladium-charcoal (10%) in methanol at atmospheric pressure, there is obtained 1-acetyl-4-hydroxy-indazole in the form of beige crystals which, after recrystallization from water, melt at 140°-142° C.

EXAMPLE 5

1-Acetyl-4-hydroxy-6-methyl-indazole.

In a manner analogous to that described in Example 4, by the hydrogenation of 1-acetyl-4-benzyloxy-6-methylindazole, there is obtained 1-acetyl-4-hydroxy-6-methylindazole in the form of pale yellowish crystals which melt at 191°–192° C.

In an analogous manner, there are obtained 1-acetyl-5-hydroxy-5-methyl-indazole (m.p. 185°–186° C.), 1-acetyl-4-hydroxy-7-methyl-indazole (m.p. 135°–136° C.) and 1-acetyl-4-hydroxy-6-ethyl-indazole (m.p. 161°–163° C.).

EXAMPLE 6

1-Acetyl-4-(2,3-epoxypropoxy)-indazole

To 17 g. 1-acetyl-4-hydroxy-indazole, dissolved in 200 ml. anhydrous dimethyl sulphoxide, there are added, while stirring, 5 g. of a suspension of sodium hydride (55–60% in paraffin) and, after termination of the evolution of hydrogen, 30 g. p-toluene-sulphonic acid 2,3-epoxypropyl ester are added thereto in 10 g. portions. The reaction mixture is heated for 2 hours at 60° C., poured into water, acidified with acetic acid and extracted with methylene chloride. The extract is washed with water, dried with anhydrous sodium sulphate, treated with fullers' earth and then evaporated to dryness in a vacuum. The residue is triturated with 100–200 ml. methanol at −40° C., filtered off with suction and then washed with methanol. There are obtained 12.5 g. 1-acetyl-4-(2,3-epoxypropoxy)-indazole in the form of colorless crystals; m.p. 83° C.

EXAMPLE 7

1-Acetyl-4-(2,3-epoxypropoxy)-6-methyl-indazole 19 g. 1-Acetyl-4-hydroxy-6-methyl-indazole, 16.4 g. epibromohydrin and 16.6 g. potassium carbonate are stirred for 20 hours at 60° C. in 100 ml. dimethyl formamide. The reaction mixture is then poured on to water and extracted with methylene chloride. The extract is dried with anhydrous sodium sulphate, treated with fullers' earth and then evaporated to dryness in a vacuum. After taking up in 100 ml. methanol, the product crystallizes. There are obtained 11.0 g. 1-acetyl-4-(2,3-epoxypropoxy)-6-methyl-indazole in the form of colorless crystals; m.p. 105°–107° C.

The following compounds are obtained in an analogous manner: 1-acetyl-4-(2,3-epoxypropoxy)-5-methyl-indazole (m.p. 75°–76° C.), 1-acetyl-4-(2,3-epoxypropoxy)-7-methyl-indazole (m.p. 108°–109° C.) and 1-acetyl-4-(2,3-epoxypropoxy)-6-ethylindazole (m.p. 77°–78° C.).

EXAMPLE 8

4-(2,3-Epoxypropoxy)-indazole

1-Acetyl-4-(2,3-epoxypropoxy)-indazole is stirred for 4 hours in a mixture of methylene chloride and liquid ammonia, using a solid carbon dioxide cooler. The reaction mixture is then evaporated in a vacuum to give a brownish oil which is pure enough for further reactions. By stirring with water, there is obtained a beige product which melts at about 60° C. (after melting, it again solidifies and then melts again at <260° C.).

EXAMPLE 9

4-(2,3-Epoxypropoxy)-6-methyl-indazole 18 g. 1-Acetyl-4-(2,3-epoxypropoxy)-6-methylindazole are stirred for 8 hours in 200 ml. methylene chloride and 100 ml. liquid ammonia. The reaction mixture is evaporated to dryness and the residue is treated with water. There are obtained 14.5 g. 4-(2,3-epoxypropoxy)-6-methyl-indazole in the form of colorless crystals; m.p. 123°–125° C. After recrystallization from methylene chloride (after cooling to −80° C.), the product melts at 138°–139° C. but the compound melts at a lower temperature in the case of a slower rate of heating.

The following compounds are obtained in an analogous manner: 4-(2,3-epoxypropoxy)-5-methyl-indazole (m.p. 76°–78° C.), 4-(2,3-epoxypropoxy)-7-methyl-indazole and 4-(2,3-epoxypropoxy)-6-ethyl-indazole.

EXAMPLE 10

4-(3-Chloro-2-hydroxypropoxy)-6-methyl-indazole

A solution of 2.7 g. 4-(2,3-epoxypropoxy)-6-methylindazole in 10 ml. glacial acetic acid is introduced, while stirring, into 10 ml. glacial acetic acid which has been saturated with hydrogen chloride at ambient temperature. After 1 hour at ambient temperature, the reaction mixture is poured into 300 ml. water and neutralised with sodium bicarbonate, a viscous oil thereby separating out, which solidifies after stirring for a comparatively long time or upon triturating with toluene. When recrystallized from toluene, with the use of fullers' earth, there is obtained 4-(3-chloro-2-hydroxypropoxy)-6-methyl-indazole in the form of colorless needles; m.p. 171°–172° C.

It will be understood that the specification and examples are illustrative but not limitative of the present invention and that other embodiments within the spirit and scope of the invention will suggest themselves to those skilled in the art.

What is claimed is:

1. Indazole compound of the formula

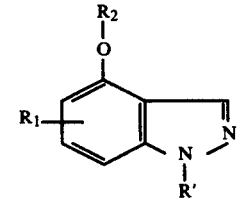

wherein $R_1$ is hydrogen or lower alkyl of up to 4 carbon atoms,

R' is hydrogen atom or alkanoyl of up to 7 carbon atom or benzoyl and $R_2$ is benzyl or a —CH.CH(Y).CH$_2$. X radical, X being an acid residue selected from hydrohalic acid and sulfonic acid radicals and Y being a hydroxyl group or X and Y together representing an oxygen atom and, when R' is an alkanoyl or benzoyl radical, $R_2$ can also be a hydrogen atom.

2. Indazole compound as claimed in claim 1 wherein $R_1$ is hydrogen.

3. Indazole compound as claimed in claim 1 wherein $R_1$ is lower alkyl of up to 4 carbon atoms.

4. Indazole compound as claimed in claim 1 wherein R' is hydrogen.

5. Indazole compound as claimed in claim 1 wherein R' is alkanoyl or benzoyl of up to 7 carbon atoms.

6. Indazole compound as claimed in claim 1 wherein $R_2$ is benzyl.

7. Indazole compound as claimed in claim 1 wherein $R_2$ is $-CH_2.CH(Y).CH_2.X$ wherein X is an acid residue and Y is a hydroxyl group.

8. Indazole compound as claimed in claim 1 wherein $R_2$ is $-CH_2.CH(Y).CH_2.X$ wherein X and Y together represent oxygen.

9. Indazole compound as claimed in claim 1 wherein R' is alkanoyl or benzoyl of up to 7 carbon atoms and $R_2$ is hydrogen.

10. Indazole compound as claimed in claim 1 namely 4-benzyloxy-6-methyl-indazole.

11. Indazole compound as claimed in claim 1 namely 4-(2,3-epoxypropoxy)-6-methyl-indazole.

12. Indazole compound as claimed in claim 1 namely 4-(3-chloro-2-hydroxypropoxy)-6-methyl-indazole.

13. Indazole compound as claimed in claim 1 namely 1-acetyl-4-hydroxy-6-methyl-indazole.

14. Indazole compound as claimed in claim 1 namely 1-acetyl-4-(2,3-epoxypropoxy)-6-methyl-indazole.

* * * * *